United States Patent
Hijikata (10) Patent No.: US 6,840,083 B2
(45) Date of Patent: Jan. 11, 2005

(54) METHOD AND APPARATUS FOR DETECTING CRACKS IN HONEYCOMB STRUCTURE

(75) Inventor: Toshihiko Hijikata, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 9 days.

(21) Appl. No.: 10/614,197

(22) Filed: Jul. 8, 2003

(65) Prior Publication Data

US 2004/0007077 A1 Jan. 15, 2004

(30) Foreign Application Priority Data

Jul. 12, 2002 (JP) ........................................ 2002-204388

(51) Int. Cl.⁷ .......................... G01P 15/00; G01N 19/08; G01N 29/04
(52) U.S. Cl. ......................................... 73/12.01; 73/799
(58) Field of Search ............................ 73/12.01–12.09, 73/760–860

(56) References Cited

U.S. PATENT DOCUMENTS

| | | |
|---|---|---|
| 3,793,874 A | 2/1974 | Shockey et al. |
| 3,906,782 A | 9/1975 | Early et al. |
| 4,319,840 A | 3/1982 | Kondo et al. |
| 4,531,400 A | 7/1985 | Nevel |
| 5,102,434 A | 4/1992 | Hijikata et al. |
| 5,275,489 A * | 1/1994 | Borneman et al. ........ 73/150 A |
| 5,419,181 A * | 5/1995 | Egan et al. ..................... 73/37 |
| 6,178,825 B1 | 1/2001 | Chang et al. |
| 2002/0035865 A1 | 3/2002 | Luk et al. |

FOREIGN PATENT DOCUMENTS

| | | |
|---|---|---|
| EP | 0 624 788 A1 | 11/1994 |
| GB | 1 085 064 | 9/1967 |

* cited by examiner

*Primary Examiner*—Edward Lefkowitz
*Assistant Examiner*—Takisha Miller
(74) *Attorney, Agent, or Firm*—Oliff & Berridge, PLC (57) ABSTRACT

A method for detecting cracks in a honeycomb structure includes the steps of: placing the honeycomb structure on the upper face of a first plate with the two end faces of the honeycomb structure facing up and down, respectively; applying to the honeycomb structure impact load adequately heavy to make powdery substance fall off the cracked portions of the honeycomb structure; and detecting the powdery substance having fallen off the cracked portions. The method enables the detection of cracks in the honeycomb structure to be simpler and easier and the honeycomb structure to be hardly damaged.

38 Claims, 6 Drawing Sheets

METHOD AND APPARATUS FOR DETECTING CRACKS IN HONEYCOMB STRUCTURE

BACKGROUND OF THE INVENTION AND RELATED ART STATEMENT

The present invention relates to a method and apparatus for detecting cracks in honeycomb structures that are used in various types of filters and catalyst carriers and, in particular, to a method and apparatus which are simple and easy and highly efficient in detecting cracks in honeycomb structures, and in addition, hardly damage the honeycomb structures.

Figure 4A:
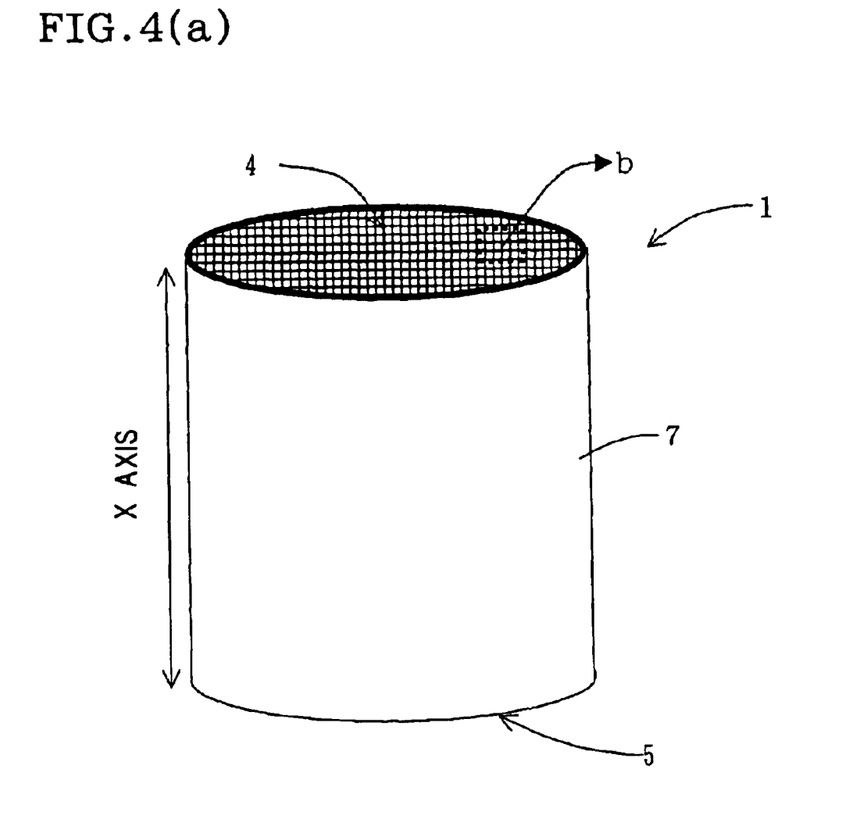
FIG. 4(a) is a schematic and diagrammatic perspective view of one example of honeycomb structures and FIG. 4(b) is an enlarged partial view of the same.
Figure 4B:
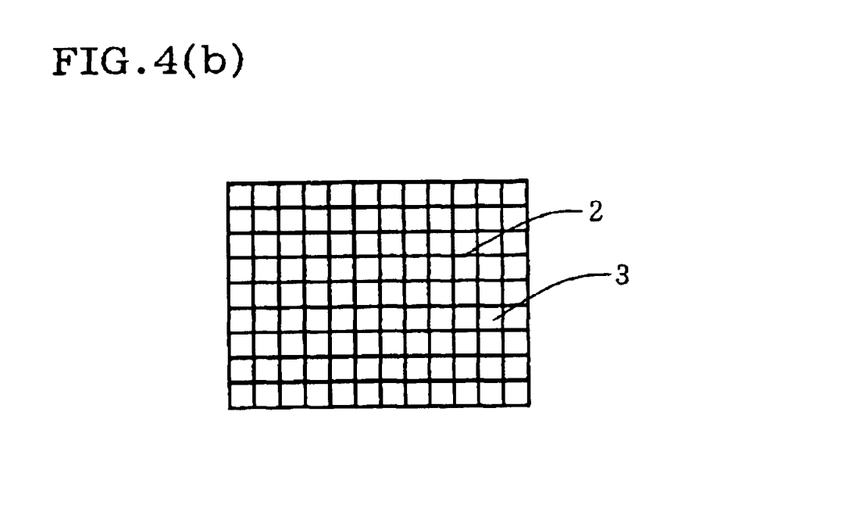

Generally, honeycomb structures are such that they are cell walled off by cell walls 2 crossing each other and have a plurality of cells 3 penetrating from their one end face 4 and to the other 5, as shown in FIGS. 4(*a*) and 4(*b*), and are often used in filters and catalyst carriers. For example, they are used in exhaust gas purifying units for heat engines such as internal combustion engine or combustion equipment such as boiler, liquid or gaseous fuel refining units, and water and sewage treatment units. They are also used as a diesel particulate filter (hereinafter referred to as DPF) to trap and remove particulate substance in dust-containing fluids such as exhaust gas exhausted from diesel engines.

Honeycomb structures used for such objects function to trap and remove unnecessary particulate substance in fluids to be treated or, where they carry catalysts on their surface, to bring fluids to be treated into contact with the catalysts, when the fluids pass through them.

Generally, honeycomb structures can be formed by bringing a powder of ceramic, metal or the like together with a binder etc. to the clay-like state, giving the clay-like mixture a honeycomb shape, and firing the honeycomb-shaped material. In this production process, defects such as crack can sometimes occur in the honeycomb structures. When cracks occur in the cell walls of the honeycomb structures, they cause deterioration in filtration efficiency and strength of the honeycomb structures and prevent the honeycomb structures from achieving good performance.

Figure 5:
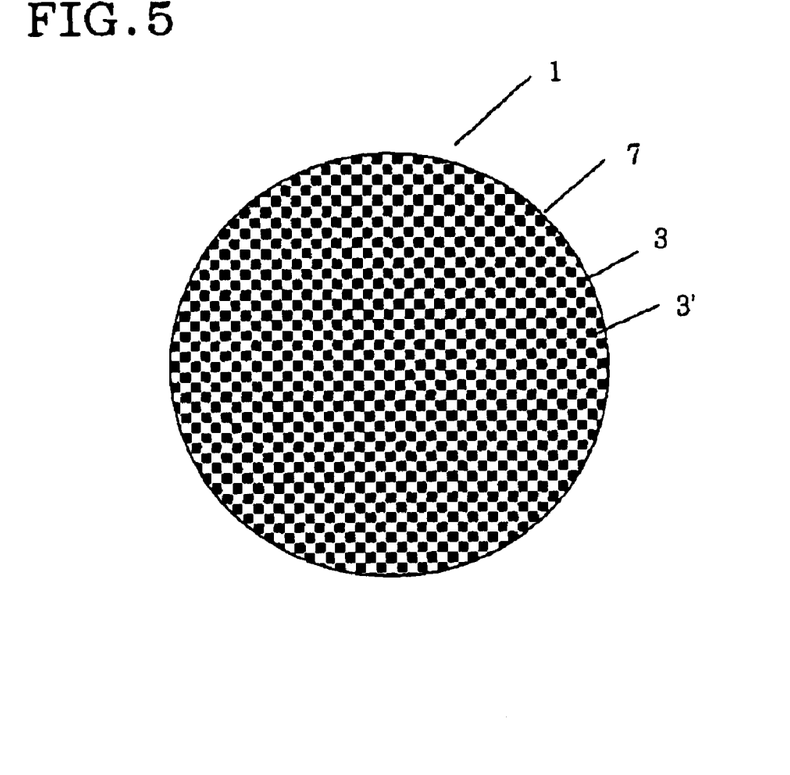
FIG. 5 is a schematic and diagrammatic plan view of another example of honeycomb structures.

The simplest method for inspecting cracks in such honeycomb structures is to inspect them visually. However, it is difficult to visually inspect cracks occurring in the cell walls of honeycomb structures. Particularly with decreasing cell wall thickness and increasing cell density of honeycomb structures in recent years, the visual inspection becomes more and more difficult. In case of a DPF, it is made up of cells 3 which are sealed up alternately, as shown in FIG. 5, and porous cell walls 2 (refer to FIG. 4(*b*)) which trap and remove particulate substance. Accordingly, cracks occurring in the cell walls 2 (refer to FIG. 4(*b*)) are difficult to observe visually from outside. In FIG. 5, the cells 3', solid black portions, indicate the plugged cells on one end face, while the cells 3, white portions, indicate the plugged cells on the other end face.

Figure 7:
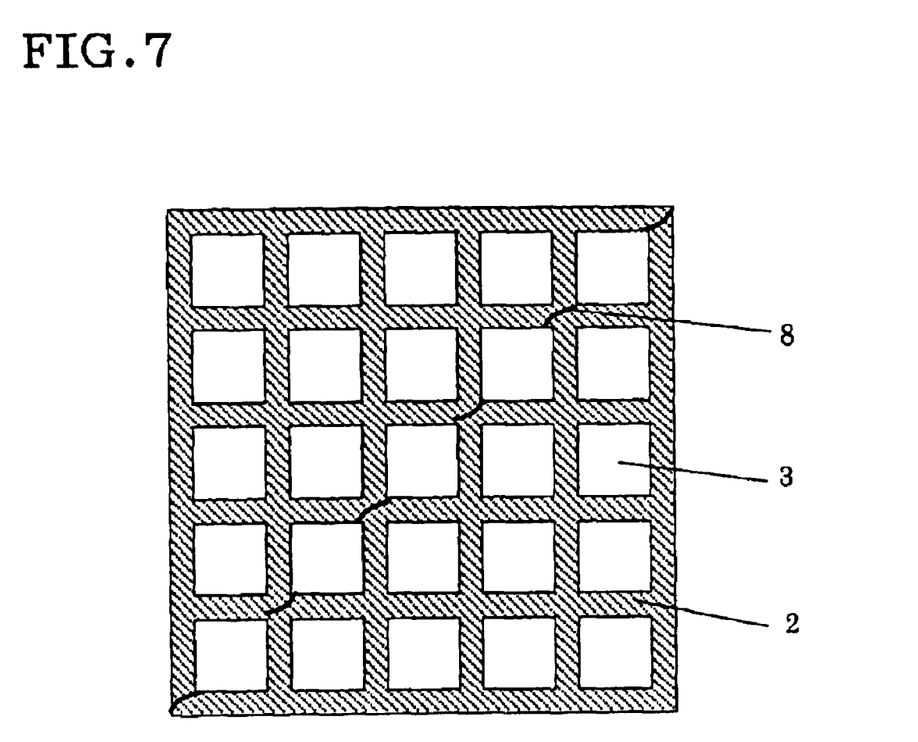
FIG. 7 is a schematic and diagrammatic view showing one example of cracks occurring in honeycomb structures.

There has been known another method, which is referred to as soot print method, for inspecting cracks in such honeycomb structures. The method is to detect cracks by flowing soot matter produced by the combustion of a diesel fuel into a honeycomb structure, for example, a DPF through its lower face, while covering the upper face of the same with white cloth, so that the soot matter discharged through the upper face adheres to the white cloth. This method is simple and easy and excels in crack detection level, but on the other hand, since it uses soot matter, it requires a step of removing the soot matter having adhered to the honeycomb structure by heat treatment after the inspection. The after-treatment of removing the soot matter requires extra time. Furthermore, the method does not allow the detection of immanent defects such as cracks not penetrating the cell walls, though it allows the detection of cracks penetrating the same. However, such immanent defects must also be detected since they are apt to grow into cracks which penetrate the cell walls when the honeycomb structure is subjected to thermal shock etc. during its use, and moreover, they contribute to the deterioration in strength of the honeycomb structure. Still further, the method does not allow the detection of cracks 8 which penetrate the plugged cells 3 on the same end face, as shown in FIG. 7.

There has been known still another method in which the presence or absence of cracks is inspected by applying air pressure to one end of a honeycomb structure while keeping the honeycomb structure in water and observing the bubbling phenomenon occurring at the other end of the honeycomb structure. In this method, though the after-treatment takes less time than in the above described soot print method, the honeycomb structure must be dried after inspection and degassed in water before inspection. These drying and degassing steps take time. Further, this method allows the detection of neither immanent defects nor cracks which penetrate the plugged cells on the same end face. The present inventors examined the use of optical and acoustic techniques in detecting cracks in honeycomb structures, but satisfactory results could not be obtained in both cases.

SUMMARY OF THE INVENTION

In light of the above described situation, the object of the present invention is to provide a method and apparatus for detecting cracks in honeycomb structures, including even such cracks as do not penetrate the cell walls of the honeycomb structures and such cracks as penetrate the plugged cells of the honeycomb structures on the same end face, the method and apparatus enabling the detection of cracks to be simpler and easier and the honeycomb structures to be hardly damaged.

First, the present invention is a crack detecting method for detecting cracks in a honeycomb structure which includes a plurality of cells penetrating itself from its one end face to the other, the method including the steps of: placing the honeycomb structure on the upper face of a first plate with the two end faces of the honeycomb structure facing up and down, respectively; applying to the honeycomb structure impact load adequately heavy to make powdery substance fall off the cracked portions of the honeycomb structure; and detecting the cracks in the honeycomb structure by detecting the powdery substance having fallen off the cracked portions.

In the detecting method of the present invention, it is preferable that the impact load is applied to the upper face of the honeycomb structure. It is more preferable that the impact load is applied to the honeycomb structure in such a manner as to dispose a second plate on the upper face of the honeycomb structure and crash an impact member into the second plate. And it is much more preferable that the impact member is crashed into the second plate by leaving the impact member to spontaneously fall to the second plate. It is also preferable that the impact load is applied after a first cushioning member is disposed between the honeycomb structure and the second plate. And it is also preferable that the area of the first cushioning member's face facing the honeycomb structure is smaller than that of the upper face of the honeycomb structure. It is also preferable that the impact load is applied after a second cushioning member is disposed between the upper face of the first plate and the lower face of the honeycomb structure. And it is also preferable that the area of the second cushioning member's face facing the honeycomb structure is smaller than that of the lower face of the honeycomb structure. It is preferable that the first and/or second cushioning member is made up of at least one kind of material selected from the group consisting of paper, rubber and plastics materials and the impact member is made up of at least one kind of material selected from the group consisting of metal, stone, ceramic and wood materials. It is also preferable that the area of the second plate's face facing the honeycomb structure is smaller than that of the upper face of the honeycomb structure and the second plate is made up of at least one kind of material selected from the group consisting of metal, stone, ceramic and wood materials. In this case, the impact load can be applied to the honeycomb structure in such a manner as to dispose a first cushioning member on the upper face of the honeycomb structure and crash the impact member into the first cushioning member. It is also preferable that the area of the upper face of the first plate is smaller than that of the lower face of the honeycomb structure and the upper face of the first plate is made up of at least one kind of material selected from the group consisting of metal, stone, ceramic and wood materials. Further, it is preferable that the color of the upper face of the first plate and/or the color of the second cushioning member is different from that of the powdery substance. And it is preferable that the impact load is applied to the honeycomb structure after a discrimination sheet having a face colored differently from the powdery substance is disposed between the lower face of the honeycomb structure and the upper face of the first plate.

Second, the present invention is a crack detecting apparatus for detecting cracks in a honeycomb structure which includes a plurality of cells penetrating itself from its one end face to the other, the apparatus including: a first plate having a upper face where the honeycomb structure is placed with its two end faces facing up and down, respectively; and impact means for applying to the honeycomb structure impact load adequately heavy to make powdery substance fall off the cracked portions of the honeycomb structure.

In the detecting apparatus of the present invention, it is preferable that the impact means applies impact load to the upper face of the honeycomb structure. It is more preferable that the detecting apparatus further includes a second plate disposed on the upper face of the honeycomb structure and the impact means includes an impact member which is crashed into the second plate. And it is much more preferable that the impact means leaves the impact member to spontaneously fall to the second plate. It is also preferable that the detecting apparatus further includes a first cushioning member disposed between the honeycomb structure and the second plate. And it is also preferable that the area of the first cushioning member's face facing the honeycomb structure is smaller than that of the upper face of the honeycomb structure. It is also preferable that the detecting apparatus further includes a second cushioning member disposed between the upper face of the first plate and the lower face of the honeycomb structure. And it is also preferable that the area of the second cushioning member's face facing the honeycomb structure is smaller than that of the lower face of the honeycomb structure. It is preferable that the first and/or second cushioning member is made up of at least one kind of material selected from the group consisting of paper, rubber and plastics materials and the impact member is made up of at least one kind of material selected from the group consisting of metal, stone, ceramic and wood materials. It is also preferable that the area of the second plate's face facing the honeycomb structure is smaller than that of the upper face of the honeycomb structure and the second plate is made up of at least one kind of material selected from the group consisting of metal, stone, ceramic and wood materials. In this case, the detecting apparatus can be made up so that it further includes a first cushioning member disposed on the upper face of the honeycomb structure and the impact means includes an impact member which is crashed into the first cushioning member. It is also preferable that the area of the upper face of the first plate is smaller than that of the lower face of the honeycomb structure and the upper face of the first plate is made up of at least one kind of material selected from the group consisting of metal, stone, ceramic and wood materials. Further, it is preferable that the color of the upper face of the first plate or of the second cushioning member is different from that of the powdery substance. And it is preferable that the detecting apparatus further includes a discrimination sheet which has a face differently colored from the powdery substance and is disposed between the lower face of the honeycomb structure and the upper face of the first plate in such a manner that the face differently colored from the powdery substance faces the honeycomb structure.

DESCRIPTION OF SYMBOLS

1 . . . Honeycomb structure, 2 . . . Cell wall, 3 . . . Cell, 3' . . . Plugged cell, 4 . . . Upper face, 5 . . . Lower face, 6 . . . Edge portion, 7 . . . Peripheral wall, 8 . . . Crack, 10 . . . Plate, 12 . . . Upper face of first second plate 14 . . . Plate, 15 . . . Lower face of second plate, 16 . . . Impact member, 18 . . . Guide, 19 . . . Discrimination sheet, 20 . . . First cushioning member, 22 . . . Lower face of first cushioning member, 24 . . . Second cushioning member, 25 . . . Upper face of second cushioning member.

DETAILED DESCRIPTION OF PREFERRED EMBODIMENT

In the following the present invention will be described in terms of its preferred embodiments; however, it is to be understood that these embodiments are not intended to limit the invention.

Figure 1:
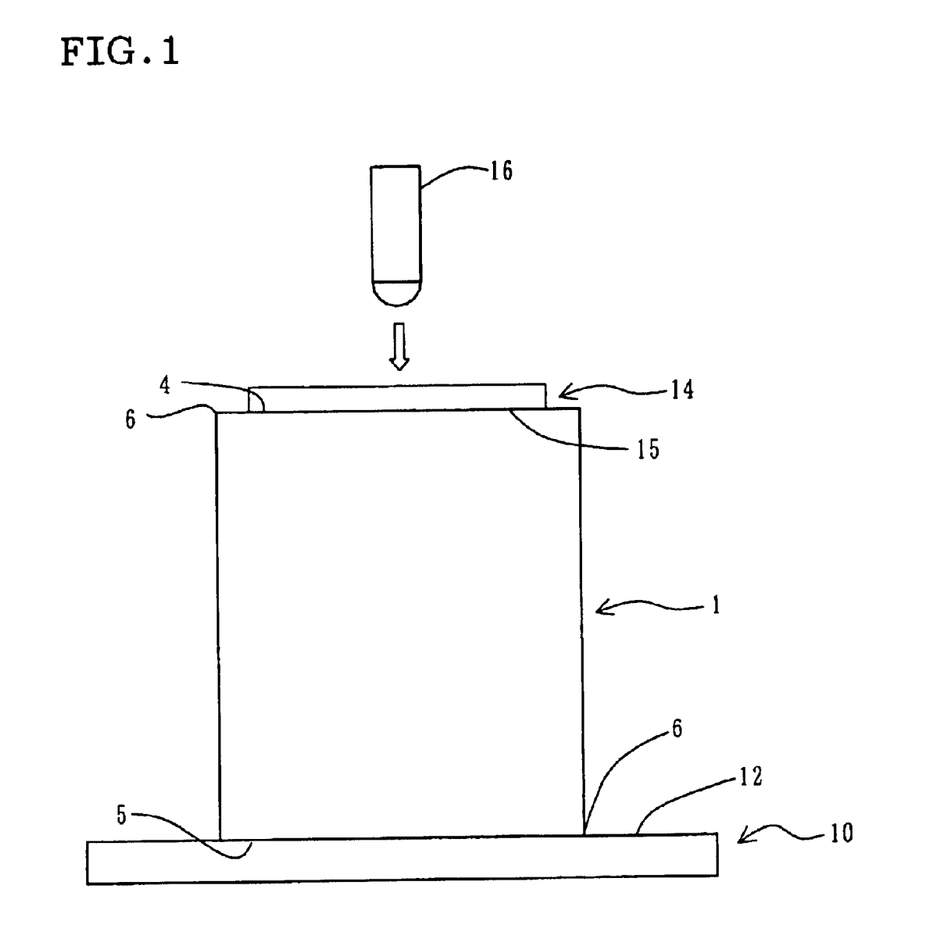
FIG. 1 is a schematic and diagrammatic front view of one example of the apparatus embodying the present invention.

First, a crack detecting apparatus of the present invention will be described. The crack detecting apparatus of the present invention includes a first first plate 10 and an impact member 16 as impact means, as shown in FIG. 1. An important characteristic of the crack detecting apparatus of the present invention is that it includes impact means for applying to a honeycomb structure 1 impact load adequately heavy to make powdery substance existing in cracks which have occurred in the honeycomb structure 1 fall downward. The cracks can be detected by ascertaining the presence of the powdery substance made to fall off the honeycomb structure by the impact means. With this apparatus, it is possible to detect even immanent defects or such cracks as penetrate plugged cells on the same end face simply and easily while avoiding the use of a large-scale apparatus.

After close examination of cracks and immanent defects in honeycomb structures, the present inventors have found that there exists powdery substance in the portions of honeycomb structures where cracks etc. have occurred and the powdery substance falls off such honeycomb structures if certain impact is applied to the honeycomb structures. It is considered that the powdery substance is part of the honeycomb structure material which has been detached from the defective or cracked portions of the honeycomb structures when cracks etc. occurred and exists in the inside of such cracks. And it is also considered that when certain impact load is applied to the honeycomb structures, particularly to the upper faces of the honeycomb structures in the compressive direction, the defects such as cracks open wider and the powdery substance falls off the honeycomb structures.

The concrete examples of the impact means in the present invention include: for example, hammering; and crashing an impact member into a honeycomb structure by swinging it like a pendulum, or by using pressure such as oil pressure, air pressure, water pressure or spring pressure, or by allowing it to spontaneously fall. Preferable impact means is means capable of applying impact load to the upper face of a honeycomb structure, and if the impact energy is the same, impact means capable of applying compressive impact load with a heavier weight is preferable in that it enables efficient detection of cracks, even smaller cracks, throughout the honeycomb structure.

When the apparatus of the present invention includes impact means which applies compressive impact load to the upper face of a honeycomb structure, it is preferable that the apparatus includes a second second plate 14 which is disposed on the upper face 4 of the honeycomb structure, as shown in FIG. 1, and the impact means includes an impact member 16 which is crashed into the second second plate 14. The use of such means inhibits the damage to the honeycomb structure 1 which is caused when applying impact load to the structure and enables the impact load to be applied relatively uniformly throughout the honeycomb structure.

Further, it is preferable that the impact means is means which leaves the impact member 16 to spontaneously fall to the second plate 14. With such means, the magnitude of the impact load can be easily controlled while changing the falling distance of the impact member 16 and be adjusted to the impact load adequately heavy to make the powdery substance fall off the honeycomb structure. The concrete examples of the impact means include, for example, the combination of the impact member 16 and a guide 18, and preferably the impact member 16 is graduated in falling distance. The impact member 16, however, can be left to fall without the guide 18 and it can be impact means independently.

Figure 2A:
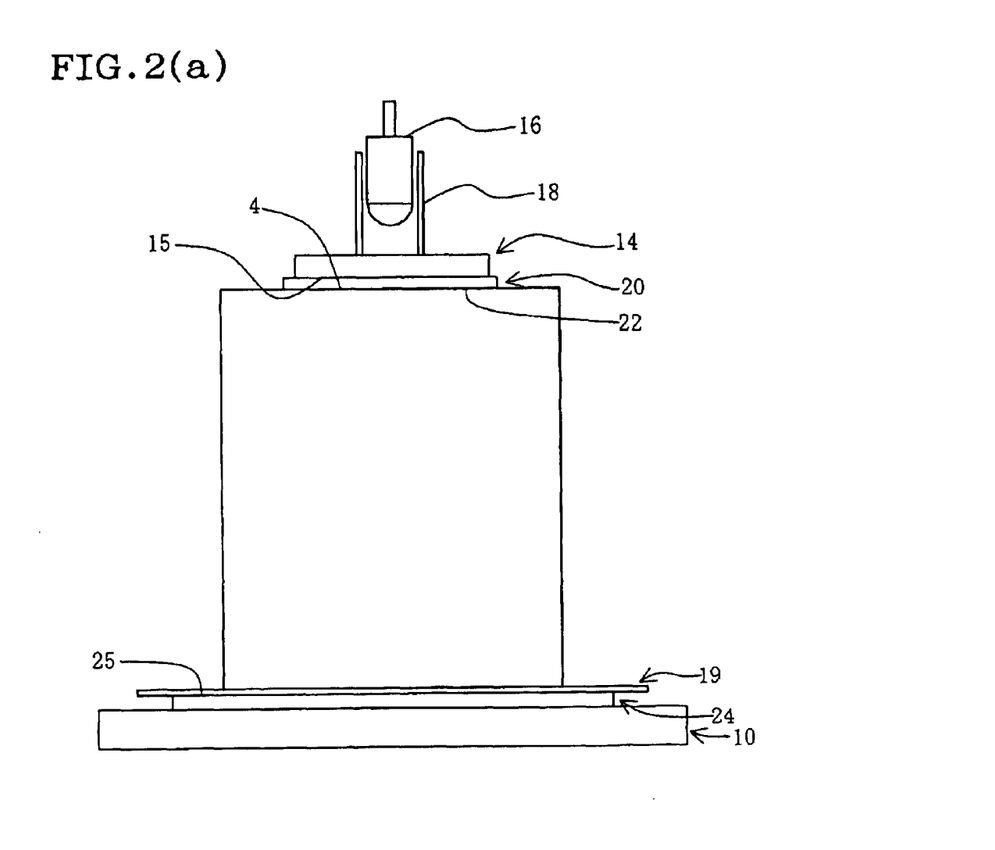
FIG. 2(a) is a schematic and diagrammatic sectional view of another example of the apparatus embodying the present invention and FIG. 2(b) is a schematic and diagrammatic plan view of the same.
Figure 2B:
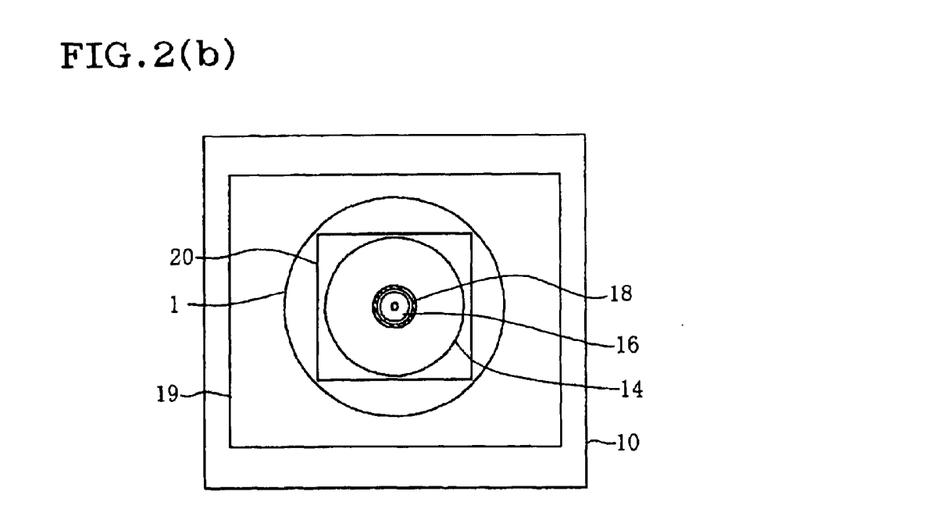

The magnitude of the impact load adequate to make powdery substance fall off a honeycomb structure varies depending not only on the material, size and shape of the honeycomb structure, but also on the cell structure such as thickness of the cell walls of the honeycomb structure and the cell density of the same porosity. Therefore, it must be established depending on the types of the honeycomb structures to be inspected. Since too heavy impact load might cause damage to a honeycomb structure, it is necessary to control the magnitude of impact load to a degree that the honeycomb structure is not damaged. The impact load can be established, using honeycomb structures where cracks have been intentionally caused by applying large thermal shock during or after their production or using honeycomb structures where cracks have been ascertained by other inspection methods, by examining the range of the impact load that makes powdery substance fall off the honeycomb structures but does not cause damage to the same with an apparatus shown in FIG. 1 or FIGS. 2(*a*) and 2(*b*) while increasing the falling distance of the impact member 16 little by little. Once the impact load is established, for the same type of honeycomb structures, it is possible to inspect the presence or absence of cracks by applying the same magnitude of impact load thereto. Thus a large number of honeycomb structures can be inspected in a short time.

The size of the second plate 14 is not particularly limited. However, taking the second plate 14 in FIG. 1 as example, it is not preferable that the area of the face on the honeycomb structure side, that is, the area of the lower face 15 of the second plate 14 is too small, because the effect of preventing damage to the honeycomb structure is decreased. It is preferable from the viewpoint of preventing damage to the edge portion 6 of the honeycomb structure that the area is smaller than that of the upper face 4 of the honeycomb structure. In other words, it is preferable that the edge portion 6 does not come into contact with the second plate. Preferably the area of the lower face 15 is 5 to 90% of that of the upper face 4 of the honeycomb structure, more preferably 20 to 90%, and particularly preferably 50 to 90%. The material of the second plate 14 is not particularly limited, either. However, relatively hard material is preferable because such material does not absorb impact load excessively. It is preferable that the material is at least one kind of material selected from the group consisting of metal materials such as aluminum, iron and stainless steel; stone materials such as natural stone and artificial stone; ceramic materials; and wood materials such as solid wood, plywood and bonded wood.

The size and material of the impact member 16 are not particularly limited, either. An impact member whose mass is adequately large to apply an appropriate impact load to a honeycomb structure can be properly selected to the types of the honeycomb structures. However, relatively hard material is preferable, like the plate described above. It is preferable that the material is at least one kind of material selected from the group consisting of metal materials such as aluminum, iron and stainless steel; stone materials such as natural stone and artificial stone; ceramic materials; and wood materials such as solid wood, plywood and bonded wood.

In the present invention, the first plate 10 includes a upper face 12 where a honeycomb structure 1 is placed with the two end faces 4, 5 of the honeycomb structure 1 facing up and down, respectively, as shown in FIG. 1. The shape and material of the first plate 10 are not particularly limited, as long as it allows the honeycomb structure 1 to be placed thereon stably. It is preferable that the upper face 12 of the first plate 10 takes shape which matches with that of the lower face 5 of the honeycomb structure so that it receives the lower face 5 stably. Further, it is preferable that the area of the upper face 12 is smaller than that of the lower face 5, in other words, the upper face 12 is so constructed that the edge portion 6 of the lower face 5 does not come in contact with the plate. This prevents the edge portion 6 of the honeycomb structure from being damaged when impact load is applied to the honeycomb structure. The term "area of the lower face" herein used means the entire area surrounded by a peripheral wall 7, including the peripheral wall 7 as well as the area of the cells 3 at the end face. As the material of the first plate 10, relatively hard material is preferable because such material does not absorb impact load excessively. It is preferable that the material is at least one kind of material selected from the group consisting of metal materials such as aluminum, iron and stainless steel; stone materials such as natural stone and artificial stone; ceramic materials; and wood materials such as solid wood, plywood and bonded wood.

In the present invention, it is preferable from the viewpoint of preventing damage to the honeycomb structure that the apparatus includes a first cushioning member 20 which is disposed between the honeycomb structure 1 and the second plate 14, as shown in FIGS. 2(a) and 2(b). Although not shown in the figures, the apparatus may be so constructed that it does not include the second plate 14, but does include the first cushioning member alone which is disposed between the honeycomb structure 1 and the second plate 14. It is also preferable from the viewpoint of preventing damage to the honeycomb structure that the apparatus includes a second cushioning member 24 which is disposed between the first plate 10 and the honeycomb structure 1. Further, it is preferable from the viewpoint of preventing damage to the edge portion 6 that the area of the face of the first cushioning member 20 on the honeycomb structure side, in other words, the area of the lower face 22 is smaller than that of the upper face 4 of the honeycomb structure. Likewise, it is preferable that the area of the face of the second cushioning member 24 on the honeycomb structure side, in other words, the area of the upper face 25 is smaller than that of the lower face 5 of the honeycomb structure. In more particular, preferably their areas are 40 to 95% of those of the upper face 4 and the lower face 5 of the honeycomb structure, and more preferably 80 to 90%. As the material for the first cushioning member 20, moderately soft material is preferable. It is preferable that the material is one kind of material selected from the group consisting of: for example, paper, rubber and plastics materials. Likewise, it is preferable that the material for the second cushioning member 24 is one kind of material selected from the group consisting of: for example, paper, rubber and plastics materials.

In the present invention, it is preferable that the apparatus includes a recording device which records the powdery substance having fallen off the honeycomb structure. The recording devices used in the invention include, for example, a camera and a video camera.

When the apparatus of this invention includes the second cushioning member, it is preferable that the color of the second cushioning member is different from that of the powdery substance, and when the apparatus of this invention does not include the second cushioning member, it is preferable that the color of the plate is different from that of the powdery substance. Doing so makes it easier to detect the powdery substance. Preferably the color difference Δ E between the second cushioning member or the plate and the powdery substance which is determined in accordance with JIS Z 8729 and 8730 is 5 or more, more preferably 10 or more, and particularly preferably 50 or more. If the color of the face where the powdery substance falls is selected so that the powdery substance is easily discriminated, the detection of the powdery substance becomes easier.

Figure 3:
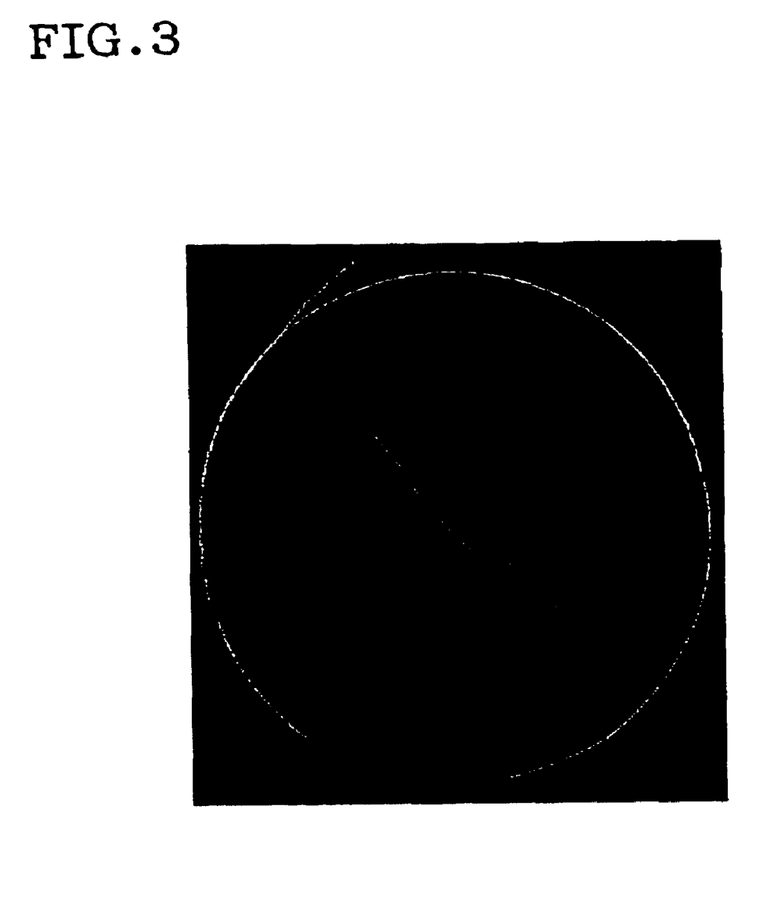
FIG. 3 is a photograph showing the position of the cracks having been detected by the present invention.

It is also preferable that the apparatus of the present invention includes a discrimination sheet 19. The discrimination sheet 19 is disposed between the first plate 10 and the honeycomb structure 1. When the apparatus of this invention includes the second cushioning member 24, it is preferable that the discrimination sheet 19 is disposed between the second cushioning member 24 and the honeycomb structure 1. Preferably the color of the discrimination sheet' face on the honeycomb structure side is different from that of the powdery substance. From the viewpoint of making the discrimination easier, preferably the color difference Δ E between the discrimination sheet' face on the honeycomb structure side and the powdery substance which is determined in accordance with JIS Z 8729 and 8730 is 5 or more, more preferably 10 or more, and particularly preferably 50 or more. FIG. 3 shows a photograph on which the powdery substance having fallen to the above discrimination sheet is marked with a color pencil and recorded. The circular line is a mark which indicates the position of the honeycomb structure and the white line-like marks inside the circular line indicates the powdery substance having fallen from cracks. According to the present invention, the presence or absence of cracks can be clearly shown and the position and length of cracks in the cross-sectional direction of the honeycomb structure can be detected.

In the present invention, the honeycomb structure, as an object where cracks are detected, includes a plurality of cells 3 which penetrate itself from one end face 4 to the other 5, as shown in FIGS. 4(a) and 4(b). The cells 3 are partitioned off by cell walls 2 and the cell walls are made up of porous material which has porous or dense material which does not have pores. The size, shape, cell wall's thickness, cell density, porosity, pore diameter, material and application of the honeycomb structure are not particularly limited, and the present invention is applicable to any kinds of honeycomb structures. However, generally the materials used for the honeycomb structures are often ceramic and/or metal, and it is preferable that the material is ceramic. The present invention is suitably applicable to the honeycomb structures where cracks are hard to detect visually because their cell walls are as thin as about 0.5 to 0.02 mm or their cell density is as great as about 15 to 240/cm$^2$. The present invention is also suitably applicable to the honeycomb structures where the adjacent cells are plugged on the opposite end faces, as in the case of DPF shown in FIG. 5.

The crack detecting method of the present invention will be described with reference to FIGS. 2(a) and 2(b). First, the honeycomb structure 1 described above is placed on the upper face 12 of the first plate 10 described above with the two end faces 4, 5 of the honeycomb structure facing up and down, respectively.

Then impact load adequately heavy to make powdery substance fall from the cracks occurring in the honeycomb structure is applied to the honeycomb structure 1. In the case shown in FIGS. 2(a) and 2(b), the impact load is applied to the honeycomb structure 1 in such a manner as to dispose the second plate 14 described above on the upper face 4 of the honeycomb structure and leave the impact member 16 described above to spontaneously fall to the second plate 14 so that the impact member 16 is crashed into the second plate 14. Compressive impact load can be applied to the upper face of the honeycomb structure by crashing the impact member 16 into the second plate 14. As a method for applying impact to the honeycomb structure, the above described impact means can be used. The impact load adequately heavy to make powdery substance fall off the honeycomb structure can be obtained through a test which uses cracked honeycomb structures and in which the magnitude of impact load is changed by changing the falling distance of the impact member, as described above.

Then the powdery substance having fallen off the honeycomb structure is detected. The powdery substance can be detected in the steps of: removing the honeycomb structure; and visually observing the powdery substance having fallen to the plate. It is preferable that the powdery substance is recorded using photography or recording devices such as cameras.

In the present invention, it is also preferable from the viewpoint of preventing damage to the honeycomb structure that impact load is applied after the first cushioning member 20 described above is disposed between the honeycomb structure 1 and the second plate 14. For the same reason, it is also preferable that impact load is applied after the second cushioning member 24 described above is disposed between the honeycomb structure 1 and the first plate 10. Although not shown in the figures, the method is applicable to the apparatus where no second plate is disposed, but the first cushioning member alone is disposed on the upper face of the honeycomb structure.

It is also preferable from the viewpoint of making the detection of powdery substance easier that impact load is applied after the discrimination sheet 19 described above is disposed between the first plate 10 and the honeycomb structure 1.

EXAMPLES

In the following the present invention will be described in more detail; however, it is to be understood that these examples are not intended to limit the invention.

To establish the detection requirements of the present invention, the impact load must be established so that it is adequately light not to cause damage to ceramic honeycomb structures and adequately heavy to enable the detection of cracks and immanent defects in the honeycomb structures. The ceramic honeycomb structures, as shown in FIGS. 5, 6, used in these examples were all obtained by using talc, alumina, kaolin, etc. as raw materials, adding water and a binder to provide a clay-like mixture, extruding the clay-like mixture using a given die (that is a die) to provide formed products, and drying and firing the formed products.

Example 1

Figure 6:
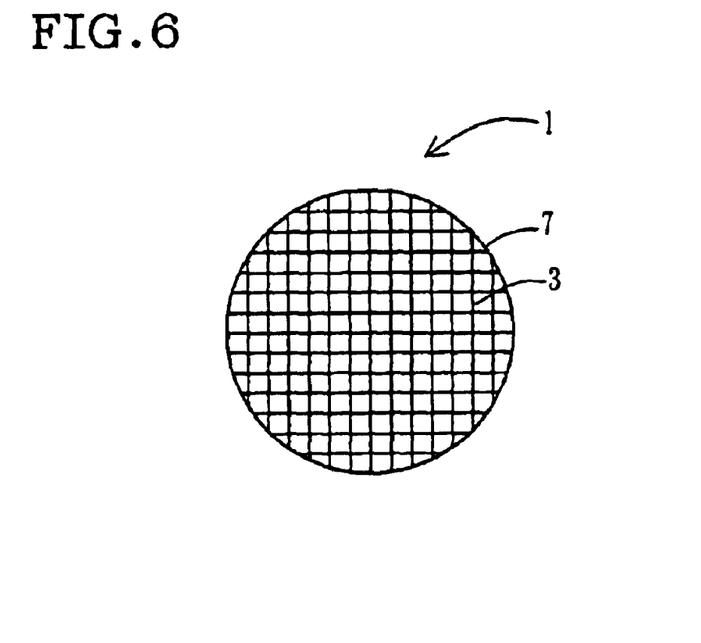
FIG. 6 is a schematic and diagrammatic plan view of still another example of honeycomb structures.

Used were cylindrical honeycomb structures 106 mm in diameter and 114.3 mm in axial length, shown in FIG. 6, which were catalyst carriers for use in exhaust gas purification used for internal combustion engine and the like and whose cell walls had a porosity of 35% and a thickness of 0.17 mm and whose cell density was 62 $cm^2$. As shown in FIG. 2, urethane rubber sheets 3 mm thick were spread as first and second cushioning members 20 and 24 on the top and lower faces of each of the honeycomb structures 1 and the honeycomb structures 1 were then placed on their respective first plates 10. A weight guide jig fitted with a metal plate 80 mm in diameter (that is a second plate) was placed on the upper face of each honeycomb structure as a guide 18 and a second plate 14, respectively, and a 940 g weight as an impact member 16 was left to fall spontaneously so that the destructive distance was obtained. The result showed that the destructive distance was 150 cm, in other words, the destructive impact energy was 13.8 N·m. Then cracks were intentionally caused inside the ceramic honeycomb structures in an electric furnace and impact load was applied to the honeycomb structures under the same conditions as above to obtain minimum impact load required to detect the cracks. The result showed that falling distances of 1 cm or more, in other words, impact energy of $0.92 \times 10^{-1}$ N·m enabled the detection of the cracks. Thus, as the impact load requirements allowing the impact load to be adequately light not to damage the honeycomb structure and to be adequately heavy to detect even smaller cracks and immanent defects, the weight was established to 940 g, the spontaneous falling distance 5.0 cm and the impact energy 0.46 N·m. Crack inspection was conducted for five samples having been subjected to burner-spalling test in accordance with the established requirements. As a result, cracks were detected in two cases among 5 samples. Then the samples were cut into 9 round slices about 10 mm thick and each of the round slices was observed under a microscope. As a result, cracks of almost the same shape and the same size as those detected by the above inspection were found inside of the two samples where cracks were detected and no cracks were observed inside the three samples where cracks were not detected. Thus the validity of the present invention and the established requirements were ascertained.

Examples 2, 3

Used were cylindrical honeycomb structures 200 mm in diameter and 200 mm in axial length, shown in FIG. 5, which were used for DPF and whose cell walls had a thickness of 0.3 mm and whose cell density was 46.5/$cm^2$. The honeycomb structures whose cell walls had a porosity of 60% were used in example 2 and that of 65% were used in example 3. As shown in FIGS. 2(*a*) and 2(*b*), urethane rubber sheets were spread as first and second cushioning members 20 and 24 on the top and lower faces of each of the ceramic honeycomb structures 1 and the honeycomb structures 1 were then placed on their respective first plates 10. A weight guide jig fitted with a metal plate 114 mm in diameter was placed on the upper face of each honeycomb structure as a second plate 14 and a guide 18, respectively, and a 940 g weight was left to fall spontaneously through the guide jig so that the destructive distance of each honeycomb structure was obtained. The results showed that the destructive distance was 30 cm, in other words, the destructive impact energy was 2.76 N·m for the honeycomb structure of example 2 and the destructive distance was 20 cm, in other words, the destructive impact energy was 1.84 N·m for the honeycomb structure of example 3. Then cracks were intentionally caused inside the ceramic honeycomb structures in an electric furnace and minimum impact load required to detect the cracks was obtained. For the honeycomb structures of example 2, a 940 g weight was used. And for the honeycomb structures of example 3, the minimum impact load was obtained under two different conditions, in other words, using a 600 g weight, a little lighter weight, and a 940 g weight since their impact destruction strength was low. The results showed that for the honeycomb structures of example 2, the cracks could be detected as long as the falling distance was 2 cm or more, in other words, the impact energy was 0.184 N·m or more, when using a 940 g weight. And for the honeycomb structures of example 3, the cracks could be detected as long as the falling distance was 2 cm or more, in other words, the impact energy was 0.184 N·mm or more, when using a 940 g weight, and the falling distances was 8 cm or more, in other words, the impact energy was 0.47 N·m or more, when using a 600 g weight. It was found that the lighter weight required the larger impact energy. This suggests that it is not impact energy but compressive force that is important for detecting cracks and immanent defects. Thus, as the impact load requirements which allow the impact load to be adequately light not to damage the ceramic honeycomb structure and to be adequately heavy to detect even smaller cracks and immanent defects to be detected, the weight was established to 940 g and the spontaneous falling distance 5.0 cm in example 2. In example 3, the weight was established not to 600 g but to 940 g, which was heavier and had a better detecting performance, and the spontaneous falling distance 3.0 cm. Internal crack inspection was conducted for 200 fired samples of each of examples 2 and 3 in accordance with the established requirements. In DPF, since their cells are plugged alternately on both end faces, in order to detect cracks which penetrate the plugged cells on the same end face, detection must be conducted on both top and lower faces. The result was such that cracks were detected in two cases among 200 samples of example 2 and in four cases among 200 samples of example 3. Then the samples were cut into 7 round slices about 25 mm thick and each of the round slices was observed under a microscope. As a result, crack-like immanent defects of almost the same shape and the same size as cracks detected by the above inspection were found inside the two samples of example 2 and inside four samples of example 3 where cracks were detected. At the same time, three were sampled among the honeycomb structures where no cracks were detected and observed under a microscope, but no abnormalities were observed in such samples. Thus the validity of the present invention and the established requirements were ascertained.

As described so far, according to the present invention, cracks in various types of ceramic honeycomb structures caused by thermal shock and crack-like defects caused during the production process could be detected at low cost and with a great accuracy by a simple apparatus. Accordingly, the use of the present invention prevents the distribution of abnormal products having thermal shock resistance abnormally or production defects and avoids damage to the honeycomb structures caused by thermal stress in actual use and production defects, whereby it can far improve the reliability and durability of ceramic honeycomb structures. Thus the method and apparatus of the present invention are very useful in inspection of honeycomb structures.

What is claimed is:

1. A method for detecting cracks in a honeycomb structure which includes a plurality of cells penetrating from one end face to another end face of the honeycomb structure, comprising the steps of:

placing the honeycomb structure on an upper face of a first plate with the two end faces of the honeycomb structure facing up and down, respectively;

applying to the honeycomb structure an impact load adequately heavy to make a powdery substance fall off of cracked portions of the honeycomb structure; and detecting the cracked portions in the honeycomb structure by detecting the powdery substance having fallen off the cracked portions.

2. The method for detecting cracks in a honeycomb structure according to claim 1, wherein the impact load is applied to the upper face of the honeycomb structure.

3. The method for detecting cracks in a honeycomb structure according to claim 2, wherein the impact load is applied to the honeycomb structure by crashing the impact load into a second plate disposed on the upper face of the honeycomb structure.

4. The method for detecting cracks in a honeycomb structure according to claim 3, wherein the impact load crashed into the second plate by allowing the impact member to fall to the second plate.

5. The method for detecting cracks in a honeycomb structure according to claim 3, wherein the impact load is applied after a first cushioning member is disposed between the honeycomb structure and the second plate.

6. The method for detecting cracks in a honeycomb structure according to claim 5, wherein an area of the first cushioning member facing the honeycomb structure is smaller than an area of the upper face of the honeycomb structure.

7. The method for detecting cracks in a honeycomb structure according to claim 5, wherein the impact load is applied after a second cushioning member is disposed between the upper face of the first plate and a lower face of the honeycomb structure.

8. The method for detecting cracks in a honeycomb structure according to claim 7, wherein an area of the second cushioning member facing the honeycomb structure is smaller than an area of the lower face of the honeycomb structure.

9. The method for detecting cracks in a honeycomb structure according to claim 5, wherein the first cushioning member is comprised of at least one kind of material selected from the group consisting of paper, rubber and plastics materials.

10. The method for detecting cracks in a honeycomb structure according to claim 7, wherein the second cushioning member is comprised of at least one kind of material selected from the group consisting of paper, rubber and plastics materials.

11. The method for detecting cracks in a honeycomb structure according to claim 3, wherein the impact load is comprised of at least one kind of material selected from the group consisting of metal, stone, ceramic and wood materials.

12. The method for detecting cracks in a honeycomb structure according to claim 3, wherein an area of the second plate facing the honeycomb structure is smaller than an area of the upper face of the honeycomb structure.

13. The method for detecting cracks in a honeycomb structure according to claim 3, wherein the second plate is comprised of at least one kind of material selected from the group consisting of metal, stone, ceramic and wood materials.

14. The method for detecting cracks in a honeycomb structure according to claim 2, wherein the impact load is applied to the honeycomb structure by crashing the impact load into a first cushioning member disposed on the upper face of the honeycomb structure.

15. The method for detecting cracks in a honeycomb structure according to claim 1, wherein an area of the upper face of the first plate is smaller than the area of a lower face of the honeycomb structure.

16. The method for detecting cracks in a honeycomb structure according to claim 1, wherein the upper face of the first plate is comprised of at least one kind of material selected from the group consisting of metal, stone, ceramic and wood materials.

17. The method for detecting cracks in a honeycomb structure according to claim 1, wherein a color of the upper face of the first plate is different from the color of the powdery substance.

18. The method for detecting cracks in a honeycomb structure according to claim 7, wherein a color of the second cushioning member is different from the color of the powdery substance.

19. The method for detecting cracks in a honeycomb structure according to claim 1, wherein the impact load is applied to the honeycomb structure after a discrimination sheet having a face colored differently from the powdery substance is disposed between the lower face of the honeycomb structure and the upper face of the first plate in such a manner that the face colored differently from the powdery substance faces the honeycomb structure.

20. An apparatus for detecting cracks in a honeycomb structure which includes a plurality of cells penetrating from its one end face to another end face of the honeycomb structure, comprising:

a first plate having an upper face where the honeycomb structure is placed with the two end faces facing up and down, respectively; and impact means for applying to the honeycomb structure an impact load adequately heavy to make a powdery substance fall off cracked portions of the honeycomb structure, wherein the powdery substance from the cracked portions indicates cracks in the honeycomb structure.

21. The apparatus for detecting cracks in a honeycomb structure according to claim 20, wherein the impact means applies the impact load to the upper face of the honeycomb structure.

22. The apparatus for detecting cracks in a honeycomb structure according to claim 20, further comprising a second plate disposed on the upper face of the honeycomb structure, wherein the impact means includes an impact member which is crashed into the second plate.

23. The apparatus for detecting cracks in a honeycomb structure according to claim 22, wherein the impact means leaves the impact member to fall to the second plate.

24. The apparatus for detecting cracks in a honeycomb structure according to claim 22, further comprising a first cushioning member disposed between the honeycomb structure and the second plate.

25. The apparatus for detecting cracks in a honeycomb structure according to claim 24, wherein an area of the first cushioning member facing the honeycomb structure is smaller than an area of the upper face of the honeycomb structure.

26. The apparatus for detecting cracks in a honeycomb structure according to claim 24, further comprising a second cushioning member disposed between the upper face of the first plate and a lower face of the honeycomb structure.

27. The apparatus for detecting cracks in a honeycomb structure according to claim 26, wherein an area of the second cushioning member facing the honeycomb structure is smaller than an area of the lower face of the honeycomb structure.

28. The apparatus for detecting cracks in a honeycomb structure according to claim 24, wherein the first cushioning member is comprised of at least one kind of material selected from the group consisting of paper, rubber and plastics materials.

29. The apparatus for detecting cracks in a honeycomb structure according to claim 26, wherein the second cushioning member is comprised of at least one kind of material selected from the group consisting of paper, rubber and plastics materials.

30. The apparatus for detecting cracks in a honeycomb structure according to claim 22, wherein the impact member is comprised of at least one kind of material selected from the group consisting of metal, stone, ceramic and wood materials.

31. The apparatus for detecting cracks in a honeycomb structure according to claim 22, wherein an area of the second plate facing the honeycomb structure is smaller than an area of the upper face of the honeycomb structure.

32. The apparatus for detecting cracks in a honeycomb structure according to claim 22, wherein the second plate is comprised of at least one kind of material selected from the group consisting of metal, stone, ceramic and wood materials.

33. The apparatus for detecting cracks in a honeycomb structure according to claim 21, further comprising a first cushioning member disposed on the upper face of the honeycomb structure, wherein the impact means includes an impact member which is crashed into the first cushioning member.

34. The apparatus for detecting cracks in a honeycomb structure according to claim 20, wherein an area of the upper face of the first plate is smaller than an area of a lower face of the honeycomb structure.

35. The apparatus for detecting cracks in a honeycomb structure according to claim 20, wherein the upper face of the first plate is comprised of at least one kind of material selected from the group consisting of metal, stone, ceramic and wood materials.

36. The apparatus for detecting cracks in a honeycomb structure according to claim 20, wherein a color of the upper face of the first plate is different from a color of the powdery substance.

37. The apparatus for detecting cracks in a honeycomb structure according to claim 26, wherein a color of the second cushioning member is different from a color of the powdery substance.

38. The apparatus for detecting cracks in a honeycomb structure according to claim 20, further comprising a discrimination sheet which has a face differently colored from the powdery substance and is disposed between a lower face of the honeycomb structure and the upper face of the first plate in such a manner that the face differently colored from the powdery substance faces the honeycomb structure.

* * * * *